(12) United States Patent
Donnelly et al.

(10) Patent No.: US 12,011,533 B2
(45) Date of Patent: Jun. 18, 2024

(54) FLUID TRANSFER DEVICE

(71) Applicant: SPOKE MEDICAL LIMITED, Leeds (GB)

(72) Inventors: Neil Patrick Donnelly, Orwell (GB); Patrick Robert Axon, Babraham (GB)

(73) Assignee: SPOKE MEDICAL LIMITED, Leeds (GB)

( * ) Notice: Subject to any disclaimer, the term of this patent is extended or adjusted under 35 U.S.C. 154(b) by 171 days.

(21) Appl. No.: 17/758,555

(22) PCT Filed: Jan. 4, 2021

(86) PCT No.: PCT/GB2021/050004
§ 371 (c)(1),
(2) Date: Jul. 8, 2022

(87) PCT Pub. No.: WO2021/140316
PCT Pub. Date: Jul. 15, 2021

(65) Prior Publication Data
US 2023/0044805 A1    Feb. 9, 2023

(30) Foreign Application Priority Data
Jan. 8, 2020   (GB) .................................. 2000249

(51) Int. Cl.
*A61M 1/00* (2006.01)
(52) U.S. Cl.
CPC ........ *A61M 1/7411* (2021.05); *A61M 1/7413* (2021.05); *A61M 1/842* (2021.05); *A61M 2205/3334* (2013.01); *A61M 2205/42* (2013.01)

(58) Field of Classification Search
CPC .. A61M 1/7413; A61M 1/774; A61M 1/7411; A61M 1/7415; A61M 1/743;
(Continued)

(56) References Cited

U.S. PATENT DOCUMENTS

| 3,335,727 A | 8/1967 | Spoto |
| 3,645,497 A | 2/1972 | Nyboer |

(Continued)

FOREIGN PATENT DOCUMENTS

| EP | 0303557 A2 | 2/1989 |
| GB | 2591087 B | 11/2023 |

OTHER PUBLICATIONS

International Search Report and Written Opinion for International Application No. PCT/GB2021/050047, dated Mar. 19, 2021, (14 pages), European Patent Office, Rijswijk, Netherlands.
(Continued)

*Primary Examiner* — Scott J Medway
(74) *Attorney, Agent, or Firm* — Alston & Bird LLP (57) ABSTRACT

The present application provides a device (100) for transferring a fluid from a surgical site, comprising an elongate body portion (102) defining a proximal end region (106) connectable to a source of negative pressure; an elongate neck portion (104) defining a distal end region (108) of the device locatable at a surgical site; a through bore (118) extending from the distal end region to the proximal end region; and a control member (116) for selectively controlling a negative pressure at the distal end region, wherein the control member comprises a valve portion (124) configured to at least partially restrict a fluid flowing along the through bore when moved from an open position towards a closed position. A system including the device for transferring a fluid from a surgical site is also provided.

17 Claims, 6 Drawing Sheets

(58) Field of Classification Search
CPC .......... A61M 1/76; A61M 1/77; A61M 1/772; A61M 16/0816; A61M 16/0875; A61M 39/10
See application file for complete search history.

(56) References Cited

U.S. PATENT DOCUMENTS

| | | | |
|---|---|---|---|
| 4,212,300 A | 7/1980 | Meals | |
| 4,299,221 A * | 11/1981 | Phillips | A61C 17/06 604/119 |
| 4,708,717 A * | 11/1987 | Deane | A61M 1/772 604/35 |
| 4,800,869 A * | 1/1989 | Nakajima | A61B 1/00068 600/158 |
| 4,878,900 A | 11/1989 | Sundt | |
| 5,046,486 A * | 9/1991 | Grulke | A61M 3/0208 601/161 |
| 5,120,305 A | 6/1992 | Boehringer et al. | |
| 5,254,083 A * | 10/1993 | Gentelia | A61M 1/774 604/35 |
| 5,295,956 A * | 3/1994 | Bales | A61M 1/7415 606/49 |
| 5,484,402 A * | 1/1996 | Saravia | A61M 1/7415 604/35 |
| 5,514,089 A * | 5/1996 | Walbrink | A61M 1/774 604/35 |
| 5,830,214 A | 11/1998 | Flom et al. | |
| 6,149,622 A | 11/2000 | Marie | |
| 6,179,807 B1 * | 1/2001 | Henniges | A61M 1/774 604/35 |
| 7,641,640 B2 * | 1/2010 | Burton | A61M 1/67 604/319 |
| 10,524,889 B1 | 1/2020 | Bordas | |
| 2002/0173744 A1 | 11/2002 | Epstein | |
| 2017/0050011 A1 * | 2/2017 | Zergiebel | A61M 39/1011 |

OTHER PUBLICATIONS

United Kingdom Search Report for Application No. GB2000249.9, dated Jun. 5, 2020, (2 pages), Intellectual Property Office, South Wales, United Kingdom.
Preliminary Examination for Great Britain Patent Application No. 2000249.9, dated Feb. 13, 2020, (2 pages), Intellectual Property Office, South Wales, United Kingdom.
Search Report for Great Britain Patent Application No. 2000249.9, dated Jun. 8, 2020, (5 pages), Intellectual Property Office, South Wales, United Kingdom.
Examination Report for Great Britain Patent Application No. 2000249.9, dated Aug. 22, 2023, (3 pages), Intellectual Property Office, South Wales, United Kingdom.
Response to Examination Report for Great Britain Patent Application No. 2000249.9, dated Aug. 30, 2023, (49 pages), Intellectual Property Office, South Wales, United Kingdom.
Intention to Grant for Great Britain Patent Application No. 2000249.9, dated Sep. 15, 2023, (2 pages), Intellectual Property Office, South Wales, United Kingdom.
Notification of Grant for Great Britain Patent Application No. 2000249.9, dated Oct. 31, 2023, (2 pages), Intellectual Property Office, South Wales, United Kingdom.

* cited by examiner

FLUID TRANSFER DEVICE

CROSS REFERENCE TO RELATED APPLICATIONS

This application is a National Stage Application, filed under 35 U.S.C. § 371, of International Application No. PCT/GB2021/050004, filed Jan. 4, 2021, which claims priority to and the benefit of Great Britain Application No. 2000249.9, filed Jan. 8, 2020; the contents of both of which as are hereby incorporated by reference herein in their entireties.

BACKGROUND

Related Field

The present invention relates to a device for transferring solids and/or fluids from a location, and in particular, but not exclusively, to a suction device for use in, for example, the medical industry during a surgical procedure.

Description of Related Art

A suction tube is often used by a surgeon or an assistant to remove fluid from a surgical site during a surgical or investigative procedure, such as an abdominal procedure or an ear, nose and throat (ENT) procedure. A conventional ENT suction tube is typically made from stainless-steel and has an outer diameter of around 1-5 mm. The tube typically extends from a plastic attachment portion for coupling the tube to a pump to create a negative pressure at a distal end of the tube. The attachment portion connects by way of an interference fit or threaded connection to a length of flexible tubing coupled to the pump. The attachment portion may be configured to allow the surgeon or assistant to hold the same and manoeuvre the suction tube in use.

However, conventional suction tube devices have no or very limited function to allow a user to efficiently, accurately and selectively control the negative suction pressure at the distal end of the tube locatable at a surgical site. Uncontrolled suction forces can cause trauma to delicate organs leading to unintended injury and patient morbidity. Furthermore, manoeuvring the suction device during a surgical procedure often causes the flexible tubing between the device and the vacuum pump to twist which in turn applies a reaction torque to the suction device itself. This reaction torque can undesirably restrict the user when manoeuvring the suction device and can result in the suction tube unintentionally rotating which could cause discomfort to the patient. In addition, conventional suction tubes are prone to blocking, particularly at the tip and around connections, e.g. between the device and the flexible tubing, when for example wax, clotted blood, bone fragments, or the like, block the tube at least partially, and often completely, which results in a significant reduction in performance of the suction device and in turn undesirable downtime of the surgical procedure, increased waste and cost.

Conventional suction devices are also typically noisy to use in view of turbulence caused within the device and the constant vacuum being applied at the distal end of the suction tube when the device is not being used. This can be frustrating and distracting to a surgeon and when the device is being used close to the ear the relatively high noise levels can cause acoustic trauma (hearing loss, hyperacusis and tinnitus) to the patient. Furthermore, conventional suction devices are uncomfortable to use for relatively long periods of time and/or during surgical procedures which require high levels of accuracy from the surgeon and/or their assistant.

BRIEF SUMMARY

It is an aim of certain embodiments of the present invention to provide a device for accurately and efficiently transferring a solid and/or fluid from a surgical site.

It is an aim of certain embodiments of the present invention to provide a suction device for use by a surgeon which is comfortable to use for relatively long periods of time.

It is an aim of certain embodiments of the present invention to provide a suction device which allows a surgeon to accurately and efficiently control the amount of suction applied by the device at a surgical site and also noise intensity.

It is an aim of certain embodiments of the present invention to provide a suction device which is easy to connect to a vacuum source, such as a pump, and which is not adversely affected by the flexible tubing coupling the device to the vacuum source.

It is an aim of certain embodiments of the present invention to provide a suction device which can be used with a selected one of a plurality of differently configured suction tubes based on the surgical procedure and/or the surgical site.

It is an aim of certain embodiments of the present invention to provide a suction device which is at least less prone to blocking and which is significantly quieter than conventional suction devices, particularly when not being used.

According to a first aspect of the present invention there is provided a device for transferring a fluid from a surgical site, comprising:
  an elongate body portion defining a proximal end region connectable to a source of negative pressure;
  an elongate neck portion defining a distal end region of the device locatable at a surgical site;
  a through bore extending from the distal end region to the proximal end region; and
  a control member for selectively controlling a negative pressure at the distal end region,
  wherein the control member comprises a valve portion configured to at least partially restrict a fluid flowing along the through bore when moved from an open position towards a closed position.

Optionally, the control member comprises a button portion selectively movable with respect to the body portion by a user holding the device to move the valve member away from the open position.

Optionally, the valve portion is moved away from the open position responsive to the button portion being pressed by the user.

Optionally, the valve portion is configured to stop fluid flow along the through bore when in the closed position.

Optionally, the button portion comprises a first abutment surface for engagement with a retaining region of the body portion when the valve portion is in the open position.

Optionally, the button portion comprises a second abutment surface for engagement with the retaining region of the body portion when the valve portion is in the closed position.

Optionally, the control member is configured to lock the valve portion in the closed position.

Optionally, the button portion comprises a third abutment surface for engagement with the retaining region of the body portion to lock the valve portion in the closed position.

Optionally, the valve portion is configured to allow fluid to flow unrestricted along the through bore when the valve portion is in the open position.

Optionally, the valve portion comprises a through hole configured to axially align with the through bore when in the open position.

Optionally, a diameter of the through hole is substantially the same as a diameter of adjacent regions of the through bore.

Optionally, the control member comprises a bore extending from a hole in an upper surface of the button portion to communicate with the through hole in the valve portion.

Optionally, the valve portion is biased towards the open position by a biasing element.

Optionally, an inner surface of the through bore tapers outwardly in a distal to proximal direction.

Optionally, an axis of the distal end region is angled with respect to an axis of the proximal end region.

Optionally, the distal end region is configured to mount an attachment portion of a suction tube thereon.

Optionally, the proximal end region comprises an annular recess for receiving one or more projections extending inwardly from an end fitting of a flexible tube coupled to a source of negative pressure.

Optionally, the proximal end region comprises a tapered outer surface for sealing engagement with a corresponding tapered inner surface of the end fitting.

According to a second aspect of the present invention there is provided a system for transferring a fluid from a surgical site, comprising:
  a device according to the first aspect of the present invention; and
  at least one nozzle mountable on the distal end region of the device.

Optionally, the at least one nozzle comprises a plurality of differently configured nozzles.

Optionally, the system comprises a flexible tube connectable to the proximal end region and rotatable with respect to the device.

Optionally, the flexible tube comprises at least one end fitting and a substantially flexible tube member comprising a tubular wall portion for transporting a fluid and a plurality of longitudinally spaced apart rib portions located at least partially around the tubular wall portion.

Optionally, adjacent ones of the rib portions are coupled together by at least one flexible hinge element.

Optionally, the hinge elements are oriented in a longitudinal direction with respect to the tube member.

According to a third aspect of the present invention there is provided use of a device according to the first aspect of the present invention or a system according to the second aspect of the present invention for transferring a fluid from a surgical site.

BRIEF DESCRIPTION OF THE FIGURES

Certain embodiments of the present invention will now be described with reference to the accompanying drawings in which:

FIG. 5b illustrates a section view of the connected system of FIG. 5a.

DETAILED DESCRIPTION OF VARIOUS EMBODIMENTS

Figure 1:
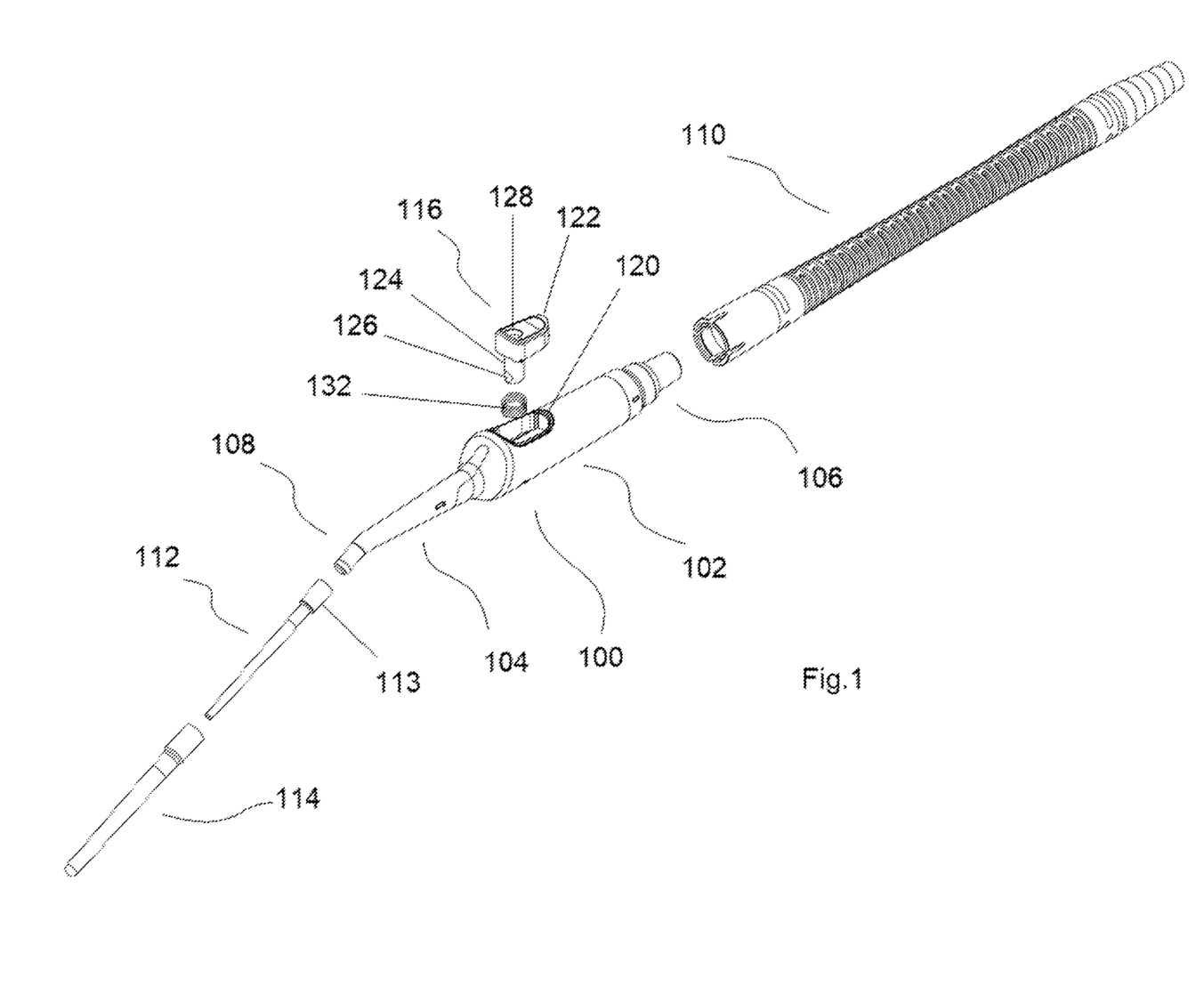
FIG. 1 illustrates a system according to certain embodiments of the present invention including a suction device, a flexible tube, a suction tube, and a suction tube cap.

As illustrated in FIG. 1, a suction device 100 according to certain embodiments of the present invention includes an elongate body portion 102 and an elongate neck portion 104 extending therefrom. The body portion 102 defines a proximal end region 106 of the device for attaching a flexible tube 110 thereto which is coupled in use to a source of negative pressure, such as a vacuum pump, and the neck portion 104 defines a distal end region 108 of the device for mounting a suction tube 112 thereto. A cap or cover 114 having a closed distal end is mountable over the suction tube 112 to protect the same and prevent ingress of dirt or the like into the tube and device when not in use. Alternatively, the distal end of the cover 114 may be open to aid manufacturing, for example. Aptly, the cover 114 provides a visual and/or tactile indication that the suction tube has been used previously on a different patient and is therefore no longer clean for use. For example, the cover may be coloured and/or may be coupled to a portion of the suction tube by a frangible region which is compromised when the cover is removed from the tube. Once the cover 114 has been removed by a first user, it is clear to a second user that the suction tube has previously been used. A control member 116 is mounted in the body portion 102 to allow a user to selectively stop, start and control the level of suction provided at the distal end of the suction tube 112 in use, as further described below.

Figure 2A:
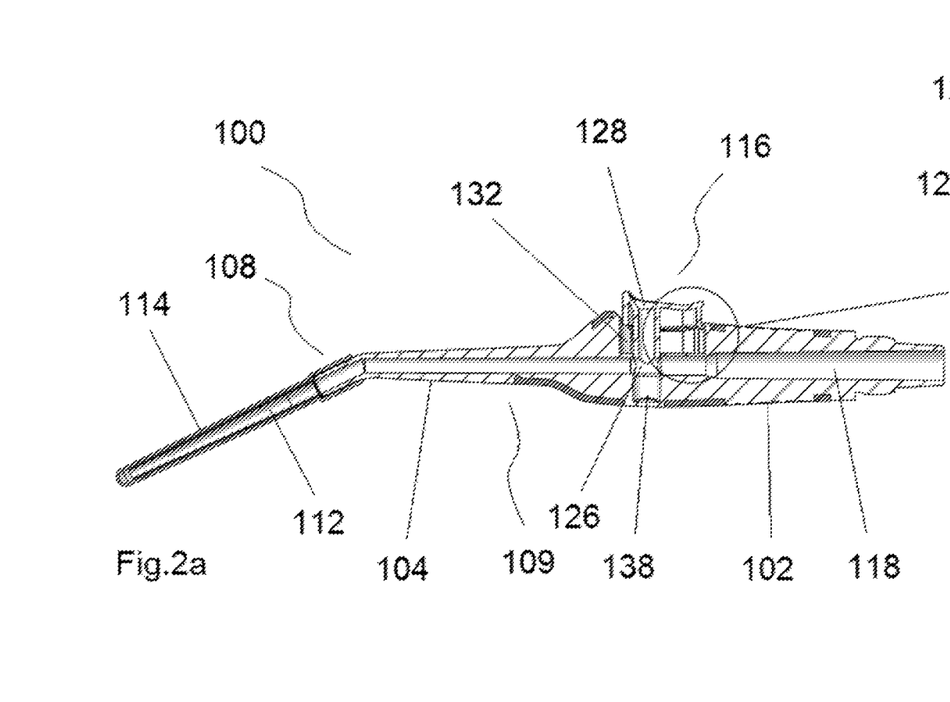
FIG. 2a illustrates a sectional view of the suction device with the suction tube and cap attached and the control member in the open position.

As illustrated in FIG. 2a, the device 100 comprises a through bore 118 extending from the distal end region 108 to the proximal end region 106 to allow a fluid to flow through the device from the suction tube 112. The through bore 118 is disposed centrally, i.e. axially, through the neck portion 104 and the body portion, and tapers gradually outwardly from the distal end region 108 to the proximal end region 106 of the device. The through bore 118 has a minimum diameter of around 2 mm and a maximum diameter of around 15 mm. This tapering of the through bore prevents the build-up of solid material, such as blood or tissue, which could undesirably lead to reduced suction or complete blockage of the through bore. The inner surface of the through bore 118 is also substantially continuous with no sudden angles, steps or gaps otherwise caused by sudden changes in wall direction and connections/joints which can lead to blockages and/or fluid turbulence and in turn compromised suction and noise. Any undesirable steps along the through bore can cause air turbulence resulting in noise and/or refuse, such as blood, being transferred from the surgical site to dry leading to blocking of the through bore.

The body portion 102 includes an aperture 120 extending from its outer surface towards the through bore 118. A hole in the base of the aperture 120 communicates with the through bore 118. The aperture 120 is configured in size and shape to accommodate an upper portion of the control member 116 which is slidably mounted therein to allow the same to move inwardly and outwardly with respect to the body portion 102.

As best illustrated in FIG. 1, the control member 116 includes a button portion 122 and a valve portion 124 extending downwardly from an under surface of the button portion 122. The button portion 122 has a side wall extending downwardly from an upper surface 130 to define a bell or cap-shaped button portion having a substantially open lower edge region. The valve portion 124 extends from a distal (forward) region of the button portion 122 and beyond the lower edge region thereof.

The valve portion 124 is substantially elongate and has a circular cross section. Alternatively, the valve portion may be substantially elliptical, hexagonal, square or the like in cross section. The valve portion 124 includes a through hole 126 proximal its lower end which corresponds in size and shape to the diameter of the through bore 118 to thereby provide a continuous and smooth bore surface when the through hole 126 of the valve portion 124 is in axial alignment with the axis of the through bore 118 when the control member 116 is in a first position, as illustrated in FIG. 2a. The through hole 126 is aptly around 7 mm in diameter but may vary depending on its location along, and/or the diameter of, the tapered through bore 118, e.g. the through hole 126 may have a diameter of around 2-7 mm. The through hole 126 and through bore 118 are substantially circular in cross section but may alternatively be elliptical or oval or the like. In the first position, the control member 116, and in turn the valve portion 124, is in an open position wherein fluid is allowed to flow unrestrained along the through bore 118 and full suction pressure is created at the distal end of the device and through the suction tube mounted thereto.

The button portion 122 is substantially elongate having curved front and aft ends, but may be oval, circular, rectangular or the like. A button portion having an elongate upper surface accommodates a user's finger or thumb and allows a user to efficiently tilt/rotate the control member slightly with respect to the body portion backwards towards the proximal end of the device, as described further below.

The button portion and valve portion are integrally formed but could be separate components coupled together. An integrally formed control member desirably reduces the number of moving/coupled parts, reduces assembly time and cost, and provides a non-complex control mechanism wherein the control member acts as a button and a valve element.

The control member 116 also includes a bore 128 extending downwardly from the upper surface 130 of the button portion 122 and along the valve portion 124 to communicate with the through hole 126 therein. The bore 128 is oriented substantially perpendicularly to the through hole 126. The bore 128 acts as a vent and allows suction pressure through the device to be further controlled by a user's thumb or finger placed at least partially over the hole in the upper surface of the button portion 122. The upper surface 130 of the button portion 122 slopes upwardly in the forward direction (towards the distal end of the device) and has upwardly curved end regions to allow the underside of a user's digit (i.e. thumb or finger) to comfortably engage and grip therewith and also to contain the digit when the control member 116 is being depressed by the user, and particularly when being urged forwardly to release the control member from the locked position as described further below.

As illustrated in FIG. 1, the control member 116 is mounted on a compression spring 132 which biases the valve portion 124 towards the open position (as illustrated in FIG. 2a). The spring is located on the valve portion 124, but the spring, or other suitable biasing element, may engage a different region of the control member 116 to urge the valve member towards the open position when no force is being applied to the button portion 122 by a user. For example, the biasing element/s may include a flexible yet resilient plastic lever, a compressible rubber or foam element, or the like. The spring/s may be a linear or progressive spring.

The control member 116 may alternatively be configured such that it is urged towards a closed position by a biasing element, such as a compression or tension spring, and the user must move the control member, and in turn the valve portion, towards the open position to selectively control a suction at the distal end of the device.

The control member 116 may alternatively be configured to slide longitudinally or rotate with respect to the body portion 102 of the device to selectively control the flow of air through the device, and in turn a suction pressure at the distal end. For example, the button portion may be a slider movable by the user's finger or thumb along a track which in turn moves the valve member with respect to the through bore to affect the flow of fluid therethrough. Alternatively, the button portion may be a knob rotatable by the user to move the through hole in the valve member out of alignment with the through bore to thereby affect the flow of fluid therethrough.

Figure 2B:
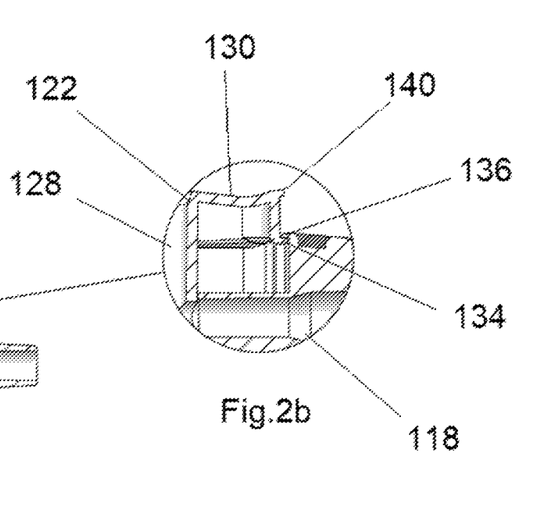
FIG. 2b illustrates a sectional close-up view of the proximal end region of the control member of the suction device when in the open position.

As illustrated in FIG. 2b, the control member 116 comprises at least one lower projection 134, such as a flange or shoulder, extending outwardly from at least a proximal and lower end region of the button portion 122 which is configured to engage with a corresponding lip region 136 extending inwardly from an upper edge region of the aperture 120 of the body portion 102. The lip region 136 acts as a stop and limits the travel of the control member 116 urged by the spring 132 to thereby couple the control member 116 to the body portion and ensure the through hole 126 therein is axially aligned with the through bore 118 when the control member 116 is in the open position. The lower projection 134 may be a plurality of spaced apart projections extending around at least a proximal end region of the button portion 122 or it may comprise a continuous flange or shoulder extending around at least the proximal end region. Aptly, the flange may extend around the periphery of the control member 116 and the corresponding lip region 136 may extend around the periphery of the aperture 120.

Figures 3A, 3B:
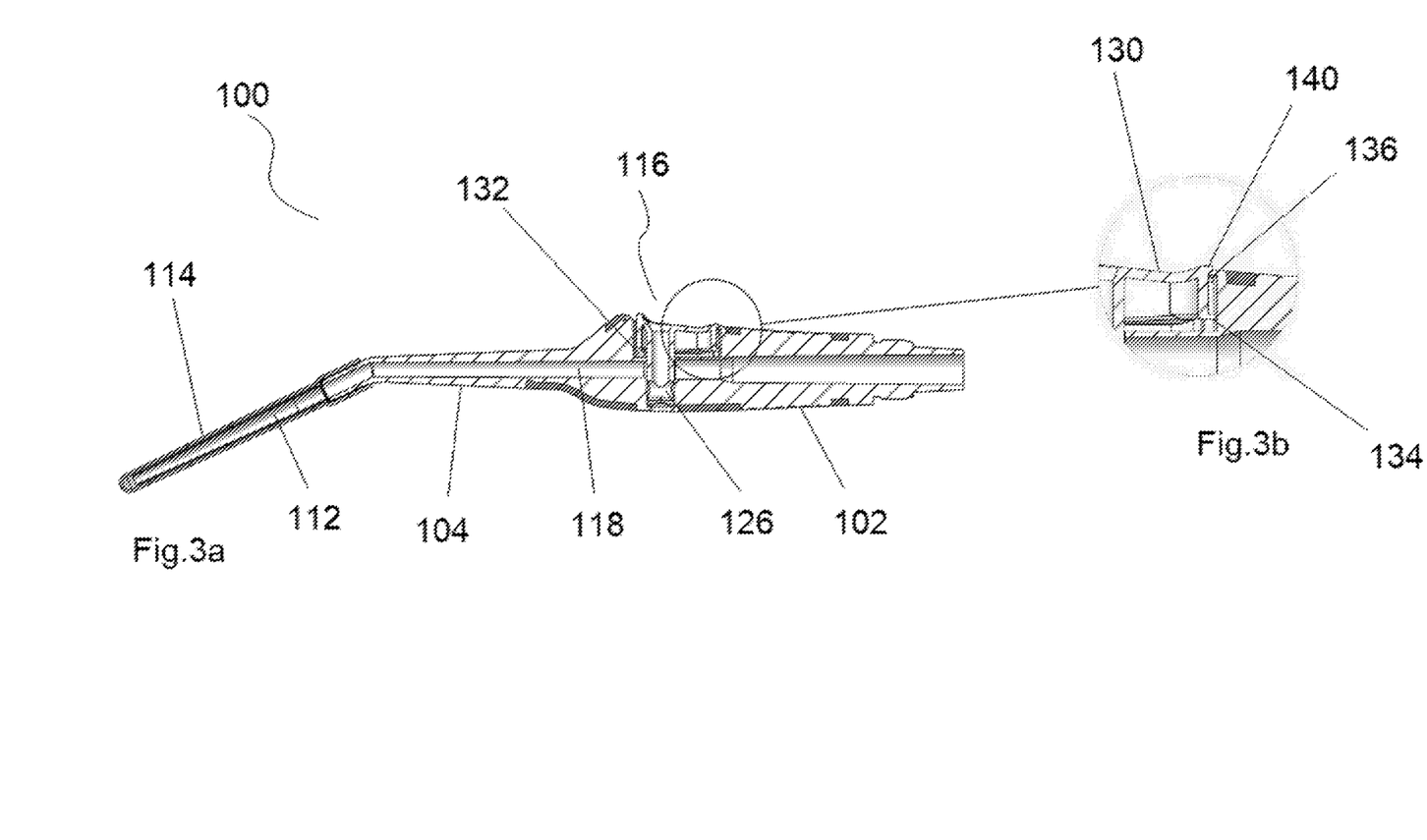
FIG. 3a illustrates a sectional view of the suction device with the suction tube and cap attached and the control member in the closed position.
FIG. 3b illustrates a sectional close-up view of the proximal end region of the control member of the suction device when in the closed position.

As illustrated in FIG. 3a, the body portion 102 of the device comprises a recess or bore 138 extending downwards and perpendicularly from the through bore 118 and axially aligned with an axis of the valve portion 124 of the control member 116. The bore 138 is configured to at least partially receive the valve portion 124 when the control member 116 is depressed by a user and moved into the body portion 102 of the device. Depressing the control member 116 compresses the spring 132 and moves the through hole 120 in the valve portion 124 downwardly and out of axial alignment with the through bore 118. The control member 116 may be depressed by a user such that the through hole 120 is partially out of axial alignment with the through bore 118 to allow a fluid to flow through the device albeit at a reduced yet still controlled suction pressure applied in the suction tube 112 mounted to the device. The suction pressure at the distal end of the suction tube 112 can thereby be accurately controlled by a user by selectively positioning the control member with respect to the body portion of the device using a digit whilst still holding and manoeuvring the device accordingly during a surgical procedure.

As illustrated in FIG. 3b, the button portion 122 of the control member 116 includes at least one upper projection 140 extending outwardly from at least a proximal and upper end region of the button portion 122 which is configured to engage with the lip region 136 extending inwardly from the upper edge region of the aperture 120 of the body portion 102. The upper projection 140 is aptly a flange region extending outwardly from the button portion 122 to define a part of the upper surface of the control member 116. When the control member 116 is depressed such that the upper flange 140 engages with the lip region 136, the upper flange acts as a stop to limit the movement of the control member into the body portion of the device. In this position, the through hole 120 in the valve portion 124 of the control member 116 is fully out of axial alignment with the through bore 118 such that no overlap exists and the lower end region of the valve member 124 engages in the bore 138 to provide a sealed interface therebetween. The control member 116 is now in a closed position and no fluid can flow through the valve member and in turn the device. Alternatively, the device may be configured such that the valve portion is urged towards the closed position when no force is exerted on the control member and the valve portion may be locked in the open position. Further alternatively, the valve member may be locked in one or both of the fully open and fully close positions and/or one of a number of different positions between the fully open and fully closed positions, such as 25%, 50% etc.

Figures 4A, 4B:
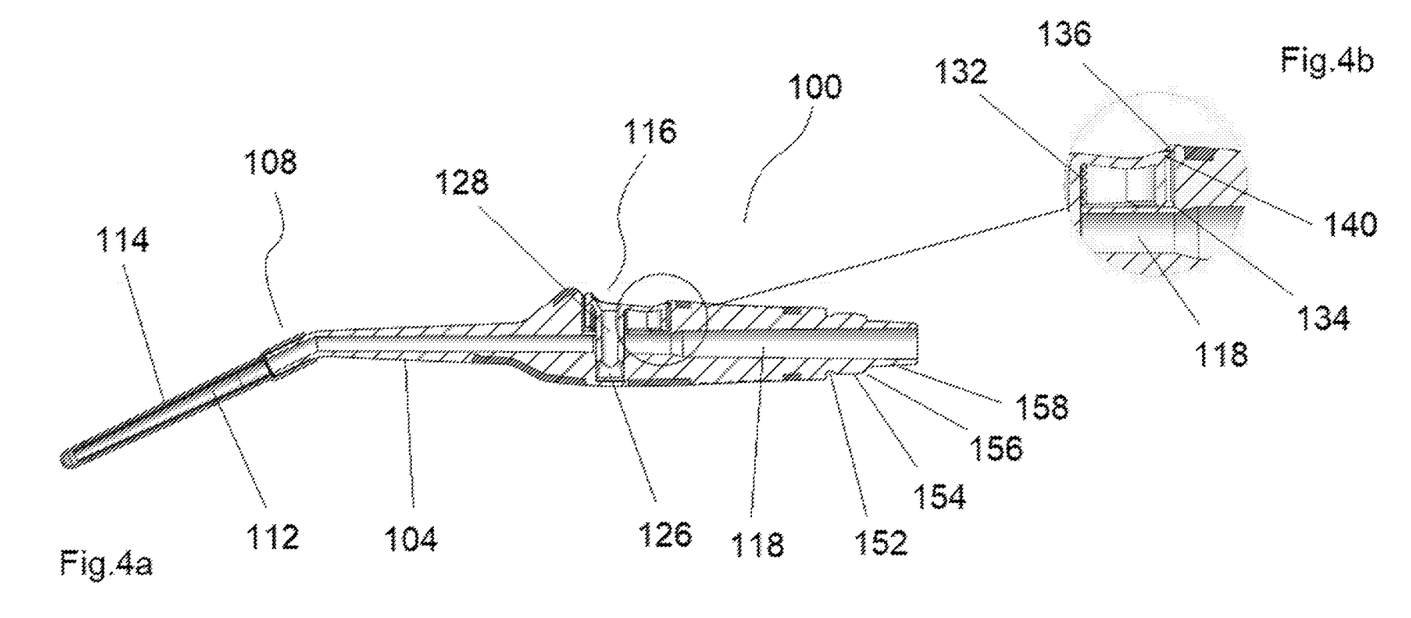
FIG. 4a illustrates a sectional view of the suction device with the suction tube and cap attached and the control member in the locked position.
FIG. 4b illustrates a sectional close-up view of the proximal end region of the control member of the suction device when in the locked position.

As illustrated in FIGS. 4a and 4b, further depression of the control member 116 into the body portion 102 of the device urges the upper flange 140 past and under the lip region 136 such that the lip region constrains the control member against the reaction force of the spring 132 and prevents it returning to the open position when a user's digit is removed. The control member 116 is now in a locked position and no fluid can flow through the valve member and in turn the device. The button portion 122 is configured to engage the base of the aperture 120 to limit its travel into the device when in the locked position. The lower end of the valve portion 124 may also engage the base of the bore 138 to also limit the travel of the control member into the device when in the locked position. Allowing the control member 116 to slightly tilt or slide in a forward-aft direction within the aperture 120 allows the upper flange 140 to be selectively moved past the lip region to lock/unlock the control member as desired. Alternatively, the upper flange 140 and/or lip region 136 may be substantially resilient and flex slightly to allow the upper flange 140 to be forced past the lip region 136 to thereby move the control member 116 from the closed position to the locked position, or vice versa. To unlock the control member 116, the same is tilted or moved forwardly by the digit of a user to thereby allow the upper flange 140 to clear the lip region 136 and in turn allow the control member to be urged towards the open position by the spring 132. Alternatively, a locking element may be movable by the user to engage with a portion of the control member, such as the button portion, to thereby lock it in the closed position. For example, a locking element may be slidably movable with respect to the body portion to at least partially cover the button portion and prevent the control member being urged towards the open position by the spring.

As illustrated for example in FIG. 2a, a central axis of the distal end region 108 of the neck portion 104 of the device is angled with respect to a central axis of a proximal region 109 of the neck portion 104. The angle is around 25 degrees, but may aptly be from 0 degrees (i.e. coaxial with the proximal region 109) to around 45 degrees, or any angle suitable for a particular surgical application. A central axis of the proximal region 109 of the neck portion 104 is substantially coaxial with an axis of the body portion 102. The central axes of the distal and proximal end regions of the neck portion may be substantially linear or they may be curved to provide a curved continuous axis extending through a substantially curved neck portion.

Providing a neck portion 104 having an angled distal end region 108 desirably allows a selected one of a plurality of suction tubes/nozzles to be mounted to the device. As illustrated, the suction tube 112 may be substantially straight. Whilst curved suction tubes having a bend therein may be used with the device, straight suction tubes 112, i.e. tubes without a bend, are relatively non-complex and inexpensive to manufacture and are also easier and less costly to sterilise or recycle than angled/bent suction tubes. Furthermore, alternatively configured attachments may be coupled to the distal end of the device, such as a straight, curved or right-angled needle, or an elongate probing device that neither sucks, blows or dispenses, for example. Such attachments may be selectively interchangeable by the user for different applications during a surgical procedure. Whilst the outer surface of the distal end region of the neck portion as illustrated is substantially circular in cross section to couple with a correspondingly shaped attachment portion of a suction tube or the like, the distal end region may alternatively be substantially square, elliptical, hexagonal or the like.

The suction tube/nozzle 112 mountable to the device according to certain embodiments of the present invention may be a one-piece stainless steel or plastics component having an attachment portion 113 configured to mount to the distal end region 108 of the neck portion 104 of the device by way of a simple inference fit, for example. An inner surface through the suction tube 112 may be tapered or parallel sided. The distal end region 108 of the neck portion 104 of the device and the attachment portion 113 of the suction tube/s 112 are configured to provide a sealed connection there between and a continuous and smooth inner wall surface to eliminate any turbulence effects, such as noise, and to prevent blocking.

Figure 5A:
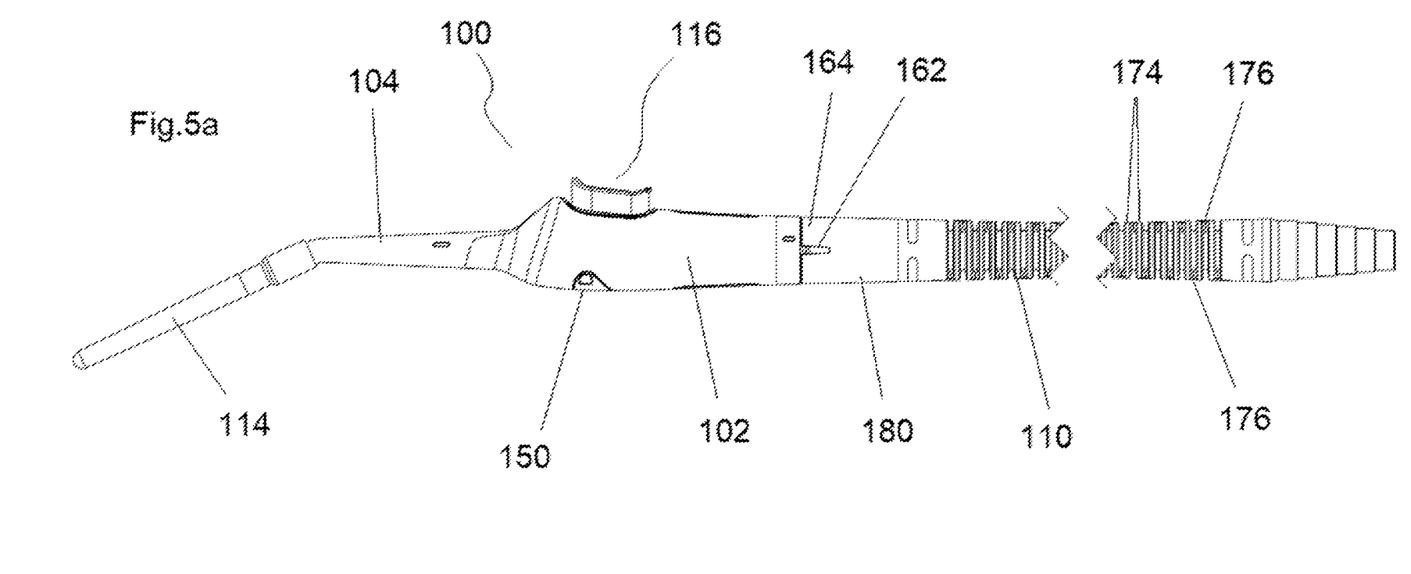
FIG. 5a illustrates the system of FIG. 1 in a connected state.

As illustrated in FIG. 5a, the device 100 includes a closure member 150 which when removed from the body portion 102 of the device exposes the bore 138 allowing the spring 132 to be inserted into the device and located over the valve portion 124 of the control member 116 during assembly. The closure member 150 can then be mounted to the body portion 102 to provide a flush outer surface of the device and close the lower end of the bore 138 and provide the base thereof. The closure member 150 may be screwed to the body portion 102 or may engage therewith by way of a snap-fit connection. The closure member 150 may be removed for cleaning/sterilising the device or to replace the spring for example. The closure member 150 may include a recess or notch which allows a tool, such as a screw driver, to prise the closure member from the body portion if a snap-fit connection is used.

The body portion 102 and the neck portion 104 are substantially circular in cross section and are integrally formed by suitable means, such as injection moulding or the like. Aptly, the body portion 102 and the neck portion 104 are formed from a plastics material such as a polycarbonate. The body portion 102 has a maximum outer diameter which is greater than a maximum outer diameter of the neck portion 104. The outer surface of the body portion 102 tapers inwardly towards the proximal end region 106 and the outer surface of the neck portion 104 tapers inwardly towards the distal end region 108. The body portion 102 is sized and shaped to ergonomically fit in a user's hand, whilst allowing the thumb or finger to comfortably engage and selectively actuate the control member 116. The body portion 102 may be formed from a material, such as a plastic or rubber, having a high coefficient of friction to the neck portion 104, or may include one or more such portions/surfaces, to provide grip to a user when holding the device. The control member 116 is aptly a one-piece component formed by injection moulding or the like. Aptly, at least the button portion 122 of the control member 116 may be formed from rubber material or the like and/or include a surface texture to provide grip when a user's thumb or finger is engaged therewith.

Figure 5B:
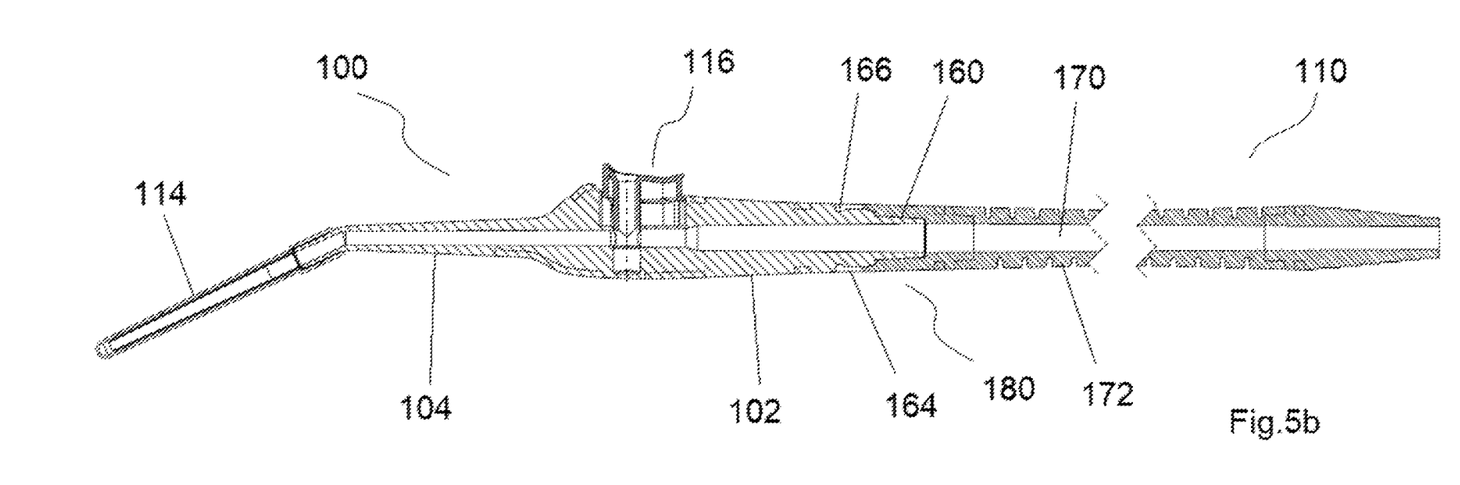

As illustrated in FIGS. 4a and 5b, the proximal end region 106 of the device 100 is configured to connect to an end fitting 180 of a flexible tube 110 according to certain embodiments of the present invention coupled to a source of negative pressure, such as a vacuum pump. The proximal end region 106 of the device comprises an annular recess 152 adjacent to an enlarged portion 154 having a tapered proximal surface 156. The proximal end region 106 tapers inwardly from the enlarged portion 154 to provide a tapered outer engagement surface 158 which terminates at a proximal end of the device.

The end fitting 180 of the flexible tube 110 comprises an inner engagement surface 160 which tapers inwardly from the open end of the end fitting 180. The angle of taper of the inner engagement surface 160 of the end fitting corresponds with the angle of taper of the outer engagement surface 158 of the device to thereby provide a sealed connection therebetween. The end fitting 180 includes a plurality of circumferentially spaced slots 162 extending in a longitudinal direction from the opening of the end fitting. These slots define spaced apart resilient end portions 164 which flex outwardly when the end fitting is urged over the proximal end region 106 of the device. The end portions 164 of the end fitting each include a projection 166, such as an annular rib, which snap into the annular recess 152 of the proximal end region 106 of the device to securely connect the end fitting to the device in a sealed manner. Alternatively, the end fitting may be a sufficiently flexible yet resilient material to expand outwardly when urged over the proximal end region 106 of the device to thereby not require the spaced apart slots 162 defining the resilient end portions 164.

The tapered proximal surface 156 acts to guide the end portions 164 of the end fitting over the proximal end region 106 of the device and urge the same outwardly until they pass the enlarged portion 154 and snap into the annular recess 152. The tapered proximal surface 156 also engages with a corresponding surface inside the end fitting to provide a further sealing interface. Desirably the circular cross section of the proximal end region 106 of the device and of the correspondingly sized and shaped end fitting 180, and in particular the snap-fit relationship between the annular recess 152 and the end fitting annular rib/s 166, allows the end fitting, and in turn the flexible tube 110, to rotate in use with respect to the device, and vice versa. This eliminates the risk of the flexible tube becoming twisted and/or exerting a reaction torque on the device during a surgical procedure. This arrangement also allows for quick connection and disconnection of the device to and from the flexible tube, and also provides a continuous and smooth transition from the device to the tube to eliminate any turbulence effects, such as noise, and to prevent blocking at the connection interface/s.

As illustrated in FIGS. 5a and 5b, the flexible tube 110 includes a relatively rigid end fitting 180 at each end of a substantially flexible tube member 170. The tube member 170 comprises a tubular wall portion 172 providing a continuous inner tube surface for transporting a fluid, and a plurality of longitudinally spaced apart annular portions 174 located on the outer surface of the tube member 170 and arranged substantially parallel to each other. Adjacent ones of the annular portions 174 are coupled together by a flexible hinge element 176. The hinge elements 176 are arranged along radially opposed sides of the flexible tube and are staggered such that a first hinge element is located on a first side of the tube, the second hinge element is located on the second side of the tube opposite the first side, the third hinge element is arranged on the first side of the tube, and so on. This arrangement allows the tube to flex is all four directions, i.e. up, down, left and right. The annular portions 174 are also relatively rigid compared to the flexible tubular wall portion 172 and protect the tubular wall portion. The rigid annular portions 174 also prevent collapse and blocking of the tubular wall portion 172 when the same is subject to a negative pressure by the vacuum source. Aptly, the tubular wall portion 172 is made from a plastics material such as a thermoplastic elastomer and the relatively rigid annular portions 174 are made from a plastics material such as a polycarbonate. The inner tubular wall portion 172 and the outer annular portions 174 may be separate parts such that the outer annular portions 174 are slidably mounted over the inner tubular wall portion 172. Alternatively, the tubular wall portion 172 and annular portions 174 may be integrally formed such as by injection moulding or additive manufacturing, or the like.

Certain embodiments of the present invention therefore provide a suction device for accurately and efficiently removing fluids from a surgical site. The suction device is comfortable to use for relatively long periods of time, and allows a user to accurately and efficiently control the amount of suction applied by the device to a surgical site, such as in the ear, nose, throat or intracranial cavity. The suction device is easy and quick to connect to a vacuum source, such as a pump, and does not cause the flexible tubing coupling the device to the vacuum source to become twisted. The suction device can be used with a selected one of a plurality of differently configured suction tubes which are inexpensive and non-complex to manufacture, sterilise or recycle. The suction device is less prone to blocking and is quieter than conventional suction devices, particularly when suction is not required.

Whilst the device according to certain embodiments of the present invention is particularly suitable as a suction device for the medical industry, the device may be suitable for non-medical applications and/or may be used as a blower device for blowing fluids or solids, such as compressed air or the like, at an object. The tapered inner bore is suitable for compressing a fluid being forced through the device and in turn increasing a pressure and flow rate of the fluid, such as air, leaving the distal end of the device. The control member is aptly configured to allow a user to accurately control the pressure and/or velocity of a fluid exiting the nozzle. The tapered nozzle is also aptly configured to accurately localise compressed air or the like at an object.

The invention claimed is:

1. A device for transferring a fluid from a surgical site, comprising:
    an elongate body portion defining a proximal end region connectable to a source of negative pressure;
    an elongate neck portion defining a distal end region of the device locatable at a surgical site;
    a through bore extending from the distal end region to the proximal end region; and
    a control member for selectively controlling a negative pressure at the distal end region when the proximal end region is connected to a source of negative pressure,
    wherein:
        the control member is slidably mounted in an aperture of the body portion to allow the control member to move inwardly and outwardly with respect to the body portion,
        the control member comprises a valve portion extending downwardly from a button portion,
        the valve portion is moveable across the through bore from an open position towards a closed position responsive to the button portion being pressed by a user to at least partially restrict a fluid flowing along the through bore,
        a biasing element urges the valve portion towards the open position when no force is applied to the button portion,
        the button portion comprises at least one upper projection extending outwardly from a proximal and upper end region of the button portion for engagement with a lip region extending inwardly from an upper edge region of the aperture,
        when the button portion is depressed, the upper projection is engageable with an upper surface of the lip region to limit said inward movement of the control member with respect to the body portion and in turn the valve portion when in the closed position,
        when the button is further depressed to urge the upper projection past and under the lip region, the upper projection is engageable with a lower surface of the lip region to constrain the control member against a reaction force of the biasing element and prevent the valve portion returning to the open position when no force is being applied to the button portion to thereby lock the valve portion in the closed position, and
        the control member is configured to tilt or move forwardly in a distal-proximal direction within the aperture to allow the upper projection of the button portion to clear the lip region and allow the control member to be urged outwardly with respect to the body portion, and in turn the valve portion towards the open position, by the biasing element.

2. The device according to claim 1, wherein the button portion comprises at least one lower projection extending outwardly from a proximal and lower end region of the button portion for engagement with the lower surface of the lip region to limit said outward movement of the control member with respect to the body portion and, in turn, the valve portion when in the open position.

3. The device according to claim 1, wherein the valve portion comprises a through hole configured to axially align with the through bore when in the open position.

4. The device according to claim 3, wherein the control member comprises a bore extending from a hole in an upper surface of the button portion to communicate with the through hole in the valve portion and act as a vent to allow a suction pressure at the distal end region of the device to be selectively controlled by a user's thumb placed at least partially over the hole.

5. The device according to claim 1, wherein an inner surface of the through bore tapers outwardly in a distal to proximal direction.

6. The device according to claim 1, wherein the distal end region is configured to mount an attachment portion of a suction tube thereon.

7. The device according to claim 1, wherein the proximal end region comprises an annular recess for receiving one or more projections extending inwardly from an end fitting of a flexible tube coupled to a source of negative pressure.

8. The device according to claim 7, wherein the proximal end region comprises a tapered outer surface for sealing engagement with a corresponding tapered inner surface of the end fitting.

9. A system for transferring a fluid from a surgical site, the system comprising:
    the device according to claim 1; and
    at least one suction tube mountable on the distal end region of the device.

10. The system according to claim 9, wherein the at least one suction tube comprises a plurality of differently configured suction tubes.

11. The system according to claim 9, comprising a flexible tube connectable to the proximal end region and rotatable with respect to the device.

12. The system according to claim 11, wherein the flexible tube comprises at least one end fitting and a substantially flexible tube member comprising a tubular wall portion for transporting a fluid and a plurality of longitudinally spaced apart rib portions located at least partially around the tubular wall portion.

13. The system according to claim 12, wherein adjacent ones of the rib portions are coupled together by at least one flexible hinge element.

14. The system according to claim 13, wherein the at least one hinge element is oriented in a longitudinal direction with respect to the tube member.

15. The device according to claim 1, wherein the at least one upper projection and/or the lip region is/are substantially resilient to flex and allow the upper projection to be urged past the lip region to selectively lock or unlock the valve portion in or from the closed position.

16. The device according to claim 1, wherein the button portion comprises a substantially elongate upper surface having upwardly curved end regions to accommodate and contain a user's thumb.

17. The device according to claim 16, wherein the upper surface of the button portion slopes upwardly towards the distal end region of the device.

* * * * *